United States Patent [19]
Goodwin, Jr.

[11] Patent Number: 5,210,021
[45] Date of Patent: May 11, 1993

[54] MULTIPLE-SITE CHEMOTACTIC TEST APPARATUS AND METHOD

[75] Inventor: Richard H. Goodwin, Jr., Bethesda, Md.

[73] Assignee: Neuro Probe, Inc., Cabin John, Md.

[21] Appl. No.: 672,561

[22] Filed: Mar. 20, 1991

[51] Int. Cl.$^5$ .................. C12Q 1/02; C12Q 1/24; C12M 1/34
[52] U.S. Cl. ...................... 435/29; 435/30; 435/284; 435/291; 435/310; 435/311
[58] Field of Search .............. 435/284, 285, 291, 310, 435/311, 29, 30

[56] References Cited

U.S. PATENT DOCUMENTS

| | | | |
|---|---|---|---|
| 3,888,770 | 6/1975 | Avital et al. | 210/238 |
| 3,929,583 | 12/1975 | Sharpe et al. | 435/301 |
| 4,317,726 | 3/1982 | Shepel | 210/236 |
| 4,493,815 | 1/1985 | Fernwood et al. | 422/101 |
| 4,514,495 | 4/1985 | Schalkowsky et al. | 435/32 |
| 4,714,674 | 12/1987 | Palladino | 435/18 |
| 4,912,057 | 3/1990 | Guirguis et al. | 435/285 |
| 5,023,173 | 6/1991 | Horwitz et al. | 435/29 |

OTHER PUBLICATIONS

W. Falk, R. H. Goodwin, Jr. and E. J. Leonard, "A 48-Well Micro Chemotaxis Assembly For Rapid And Accurate Measurement of Leukocyte Migration," (1980), pp. 239-247, Journal of Immunological Methods, 33.

L. Harvath, W. Falk and E. J. Leonard, "Rapid Quantitation of Neutrophil Chemotaxis: Use of a Polyvinylpyrrolidone-Free Polycarbonate Membrane in a Multiwell Assembly," (1980), pp. 39-45, Journal of Immunological Methods, 37.

K. L. Richards and J. McCullough, "A Modified Microchamber Method For Chemotaxis and Chemokinesis," (1984), pp. 49-62, Immunological Communications, 13(1).

W. Falk, L. Harvath and E. J. Leonard, "Only the Chemotactic Subpopulation of Human Blood Monocytes Expresses Receptors for the Chemotactic Peptide N-Formylmethionyl-Leucyl-Phenylalanine," May 1982, pp. 450-454, Infection and Immunity.

L. Harvath and E. J. Leonard, "Two Neutrophil Populations in Human Blood with Different Chemotactic Activities: Separation and Chemoattractant Binding," May 1982, pp. 443-449, Infection and Immunity.

"Neuro Probe 48 Well Micro Chemotaxis Chamber Manual," 1980.

Neuro Probe, Inc. Sales Brochure, "48 Well Micro Chemotaxis Chamber", 1988.

Neuro Probe, Inc. Sales Brochure, "12 Well Chemotaxis Chamber", 1988.

Neuro Probe, Inc. Sales Brochure, "12 Well Manifold Chamber", 1988.

Neuro Probe, Inc. Sales Brochure, "10 Well Chemotaxis Chamber", 1988.

Neuro Probe, Inc. Sales Brochure, "Blind Well and Boyden Chambers", 1988.

Neuro Probe, Inc. Sales Brochure, "Single Well and Four Well Separation Chambers", 1988.

Neuro Probe, Inc. Sales Brochure, "Three Tiered Chamber", 1988.

Neuro Probe, Inc. Sales Brochure, "Zigmond Chamber", 1988.

Neuro Probe, Inc. Sales Brochure, "Guirguis Chamber", 1988.

Neuro Probe, Inc. Sales Brochure, "Accessories", 1988.

Primary Examiner—Robert J. Warden
Assistant Examiner—T. A. Trembley
Attorney, Agent, or Firm—Kirkland & Ellis

[57] ABSTRACT

A simple chemotactic apparatus and method wherein surface tension is used to hold cell suspensions, chemotactic factors, and control fluids in place on membrane filters. In some embodiments, chemotaxis factors and controls are placed on one side of a membrane filter, and cell suspensions are placed on the other. Gravitational flow is limited by the effect of surface tension on the fluids. In some of the preferred embodiments, grids, sheets, or occluding materials are used to further limit the gravitational fluid flow.

43 Claims, 5 Drawing Sheets

MULTIPLE-SITE CHEMOTACTIC TEST APPARATUS AND METHOD

BACKGROUND

1. Field of the Invention

The present invention relates to chemotactic chambers, i.e., to chambers for measuring the effect of concentration gradients of mobile chemicals upon the directional response of biological cells. More specifically, the present invention relates to chemotaxis test sites comprising top and bottom regions separated by one or more membrane filters.

2. Background of the Invention

Chemotaxis is the directional response of biological cells or organisms to concentration gradients of mobile chemicals. Conventional chemotactic chambers comprise two compartments separated by a filter, with one or both of the compartments open to air. Cells in suspension are placed in the upper compartment, and a chemotactic factor or control is placed in the bottom compartment. The chemotactic factor can be used in various dilutions to get a dose-response curve. The controls are generally of two kinds: *negative*, when the same medium is used to suspend the cells above and below the filter; and *chemokinetic*, when a chemotactic factor is placed in the same concentration in the medium with the cells and on the opposite side of the filter. Chemokinetic controls allow the user to distinguish heightened random activity of the cells, due to contact with the chemotactic factor, from directional response in a concentration gradient of the chemotactic factor.

Chemotactic activity is measured by first establishing a stable concentration gradient in the chemotactic chamber. The chamber is incubated for a predetermined time, then the filter is removed from the apparatus. The cells that have migrated through the filter (or into the filter to a certain depth) are then counted. A comparison is then made between the activity of the cells in a concentration gradient of the chemotactic factor being tested, and the activity of the cells in the absence of the concentration gradient.

The apparatus can also be used to measure the response of cells of different origins—e.g., immune cells from patients suffering from diseases—to a chemotactic factor of known chemotactic activity. In this case the cells in question are challenged by both a negative control and the chemotactic factor to see if the differential response is depressed or normal.

Microchemotaxis chambers and some of their applications are described in Falk et al., "A 48 Well Micro Chemotaxis Assembly for Rapid and Accurate Measurement of Leukocyte Migration," *Journal of Immunological Methods*, 33, 239–247 (1980); Harvath et al., "Rapid Quantification of Neutrophil Chemotaxis: Use of a Polyvinylpyrrolidone-free Polycarbonate Membrane in a Multiwell Assembly," *Journal of Immunological Methods*, 37, 39–45 (1980); Richards et al., "A Modified Microchamber Method for Chemotaxis and Chemokinesis," *Immunological Communications*, 13 (1), 49–62 (1984); Falk et al., "Only the Chemotactic Subpopulation of Human Blood Monocytes Expresses Receptors for the Chemotactic Peptide N-Formylmethionyl-Leucyl-Phenylalanine," *Infection and Immunity*, 36, 450–454 (1982); and Harvath et al., "Two Neutrophil Populations in Human Blood with Different Chemotactic Activities: Separation and Chemoattractant Binding," *Infection and Immunity*, 36 (2), 443–449 (1982), all of which are hereby expressly incorporated by reference herein.

SUMMARY OF THE INVENTION

The present invention is a multiple-site chemotactic test apparatus comprising a membrane filter having areas which hold the fluid on the top and bottom of the filter by surface tension.

In some embodiments of the present invention, the membrane filter is a capillary pore membrane. The pores in the capillary pore membrane filter are between 0.1 and 14 micrometers in diameter, depending on the type of cell which is being used in the assay, and the nature of the assay. For example, a 0.1 or 0.2 micrometer pore size can be used to allow the pseudopods of certain cells (e.g., cancer cells) to penetrate the membrane in response to a chemotactic factor, but preclude the cell bodies from getting through the membrane. The differential response is then measured by determining how much the pseudopods protrude in stimulated as opposed to unstimulated "wells." However, if very large cells are used, and the assay is read by counting migrated cells, then the pores must be large enough for those cells to migrate through the pores.

Initially, the fluid on top of the filter is comprised of cells suspended in media (i.e., cells in a balanced salt and nutrient solution), and the fluid on the bottom of the filter is either just media (a negative control) or a solution of chemotactic factor and media. Chemokinetic controls, however, contain the same concentration of chemotactic factor above and below the filter (i.e., chemokinetic controls differ from the chemotaxis test sites because there is no *gradient* in the concentration of the chemotactic factor). In its simplest form, the test apparatus consists of a sheet of membrane filter, typically 6 to 30 micrometers thick, attached to a rigid frame. The pores in the membrane are usually chosen to be between 2 and 14 micrometers. However, when cell bodies must be prevented from migrating, smaller pore sizes are used. Drops of chemotactic factor and drops of control are placed on one side of the filter in a well-defined pattern, e.g., 96 spots, 9 mm apart in a 12×8 array. The filter and frame are then turned over, and drops of a cell suspension are pipetted onto the other side, on spots corresponding to the initial placement of the chemotactic factors and controls. The drops can range in volume from 2 to 75 μl. The drops of fluid are held in place by surface tension. Gravity induces top-to-bottom flow after fluid is placed on both sides of the filter until the surface tension forces equal the gravitational forces. The fluid on both sides of the filter is held in place by capillary action and surface tension. The apparatus is then incubated at 37°±1° C., for periods ranging from 15 minutes to 72 hours.

When the filter and the frame are removed from the incubator, several different protocols can be followed, depending on whether one or two filters are employed, and what type or types of filters are used. One protocol appropriate to an apparatus comprising a single capillary pore membrane filter is to remove the cells from the non-migrated side of the filter and then fix, stain and count the cells that have migrated through the filter. Another protocol is to fix all the cells and then count the ones that have migrated. The migrated cells are counted on the bottom side of each exposed filter area and a comparison is made between the activity of the cells exposed to the chemotactic factor and the activity of the cells exposed to the controls. If a non-capillary pore membrane is used, such as a cellulose nitrate filter, then the distance the cells have travelled into the filter matrix, i.e., the distance between the leading front of migrating cells in the filter matrix and their starting point on the surface of the filter is measured. If two filters are used, the top filter is discarded and the cells on the bottom filter are counted. Cells can also be labelled with a radioisotope such as $Cr^{51}$, and then the amount of radioactivity can be measured at each site of the bottom filter, after discarding the top filter.

Many different stains and staining techniques can be used, including, for example, fluorescent stains.

Further embodiments of the invention discussed herein incorporate features for stabilizing concentration gradients at the sites where chemotactic factors or controls and cell suspensions are placed on the filter by blocking or inhibiting gravity-driven flow of the fluids through the filter at those sites.

A first object of the present invention is to provide a simple apparatus and method for the measurement of the chemotactic activity of a plurality of specimens.

A further object of the present invention is to provide an inexpensive and/or disposable multiple-site chemotactic test apparatus.

A still further object of the present invention is to provide a multiple-site chemotactic test apparatus requiring very small volumes of cell suspension for the precise measurement of chemotactic factor activity.

An additional object of the present invention is to provide a high sensitivity multiple-site chemotactic test apparatus.

DETAILED DESCRIPTION OF THE INVENTION

Figure 1:
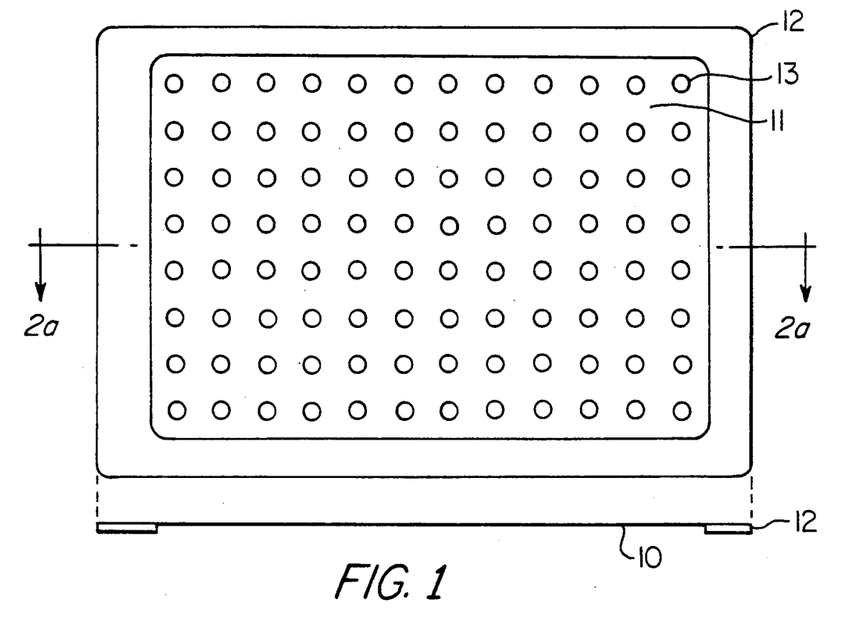
FIG. 1 is a schematic representation of a first embodiment of the chemotactic apparatus of the present invention.

In its simplest embodiment, shown in FIG. 1, the multiple-site chemotactic test apparatus 10 of the present invention comprises a membrane filter 11 (e.g., a 10 $\mu$m thick polycarbonate capillary pore membrane filter with 5 $\mu$m holes manufactured by Poretics or Costar Nucleipore, Pleasanton, Calif.) attached to a rigid frame 12, as shown in FIG. 1. The term "site" is used herein to refer to a delineated spot on a filter where a solution of chemotactic factor or plain media is positioned, and juxtaposed thereto, on the opposite side of the filter, a suspension of cells is positioned, whether these fluids are kept in position by compartments, as in conventional chemotactic chambers, or by surface tension. The position of the chemotaxis test sites is defined by, for example, a pattern 13 on filter 11. The pattern, which identifies the sites of the chemotaxis test sites, may be formed by ink imprinted on the filter, may be a patterned film of plastic or silicone, or it may be defined by a hydrophobic coating silk-screened or otherwise applied to the filter. In this first preferred embodiment of the present invention, the chemotactic fluids are kept in position by surface tension. The frame can be plastic, stainless steel, aluminum, or another suitable material. The frame must be rigid enough to keep the filter and any grids attached thereto flat. The membrane filters can be attached to the frame by any suitable fastening means, including glue, heat seals, ultrasonic seals, or mechanical means.

Figure 2A:
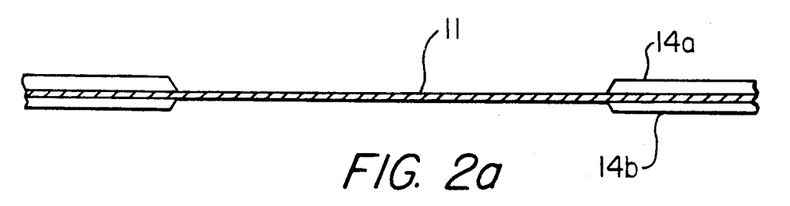
FIGS. 2a-2d are enlarged views of a portion of the chemotactic apparatus of the present invention, showing a single chemotaxis test site, at different stages of the procedure.
Figure 2B:
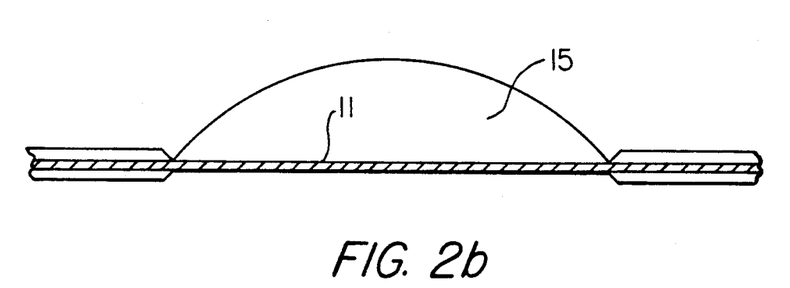
Figure 2C:
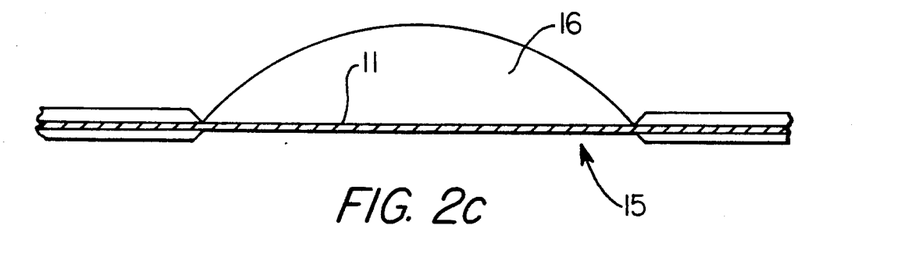
Figure 2D:
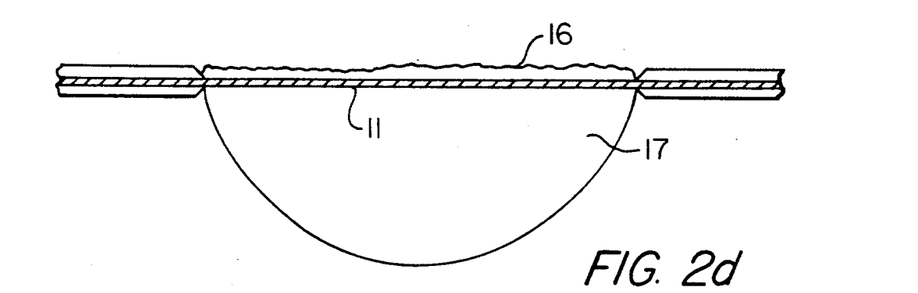

FIGS. 2a-2d are enlarged views of a portion of the chemotactic apparatus, showing a single chemotaxis test site at successive stages of the procedure. In the embodiment shown in FIGS. 2a-2d, the pattern on filter 11 is formed by hydrophobic coatings 14a on the top side and 14b on the bottom side of filter 11. The hydrophobic coatings cover the entire filter, except at the locations defining the chemotaxis test sites. In this manner, fluid transport through the filter is only possible at these locations. FIG. 2a shows the chemotaxis test site before the addition of any fluids. FIG. 2b shows the chemotaxis test site after the addition of the chemotactic factor or control 15. FIG. 2c shows the chemotaxis test site after it has been turned over, and a cell suspension 16 has been added to the side of filter 11 opposite to the chemotactic factor or control 15, before the fluid has stabilized. FIG. 2d shows the chemotaxis test site after the fluids have stabilized, when the gravitational forces have been equalled by the surface tension forces. In FIG. 2d, the fluid 17 on the bottom side of filter 11 now includes media that has flowed to that side of the filter from the cell suspension on the opposite side.

The apparatus is used according to the following procedure. Drops of various control solutions and drops of chemotactic factor (sometimes at varying concentrations) are placed on one side of the membrane filter in a well-defined pattern delineated by printing on or otherwise applied to the surface of the membrane, or by silk-screening or depositing a coating on the membrane. The coating may simply define the locations of the chemotaxis test sites, or it may also function as a hydrophobic barrier, spatially restricting the chemotactic fluid. The apparatus is then turned over, and the cell suspension is pipetted onto the corresponding spots on the opposite side. In some embodiments, gravity induces flow from the cell-suspension side of the membrane until capillary and other surface tension forces come into equilibrium with the gravitational forces. In other embodiments, surface tension and capillary action forces prevent gravity-induced flow.

The apparatus is then incubated at 37° C. for a predetermined time period, typically in the range of 15 minutes to 72 hours, depending upon the nature of the cells, the membrane filter used, the chemotactic factors being tested, etc. After incubation, cells that have not migrated from the cell-suspension side of the filter are usually removed by one of several techniques including squeegees, wiper blade and cotton swabs. This procedure is repeated after immersing the filter in a phosphate-buffered saline solution between wipings. If a double filter barrier is used, the filter with the non-migrated cells is usually discarded. Sometimes, however, the non-migrated cells are not removed, allowing them to be studied or counted as well as the migrated cells. For example, cells on one side of a polycarbonate capillary pore membrane filter 10 micrometers thick can be examined and counted using confocal microscopy without visual interference by the cells on the opposite side of the membrane.

The cells in or on the filter are then fixed (e.g., for about 2 minutes in methanol) and allowed to dry (sometimes the filter is mounted on a glass slide, and dried). The cells on the mounted filter are then stained, if necessary (e.g., with DiffQuick, manufactured by Harleco, Gibbstown, N.J.). The number of cells that have migrated through or into the filter in each test site are then counted. The cells can be counted individually using a microscope (e.g., with a 25× objective), or the number of cells could be estimated using specialized equipment such as an optical density reader (e.g., a UVmax Model optical density reader manufactured by Molecular Devices, Menlo Park, Calif. or by Optomax Image Analyzer manufactured by Optomax, Inc., Hollis, N.H.). If the cells are labeled with a radioactive isotope, the test sites are separated from each other and counted using a scintillation counter.

When this first embodiment of the apparatus of the present invention is used, obtaining the proper placement of the drops on the membrane filter can be accomplished with a hand-held pipette, an automatic variable-volume pipetter, or by an automatic pipetting machine. As shown in FIG. 1, the spacing and position of the drops of chemotactic fluid, i.e., the position of the individual chemotaxis test sites, is indicated by pattern 13. The position and spacing of the 96 chemotaxis test sites is preferably a standard spacing, e.g., the standard spacing for 96-well microtiter plates, and the outside dimensions of the frame are preferably identical to the dimensions of standard microtiter plates, so that automatic equipment such as the UVmax optical density reader can be used.

Figure 3A:
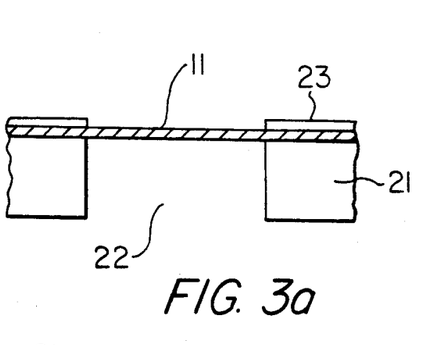
FIGS. 3a-3d are schematic representations of a second embodiment of the present invention showing the use of a grid positioned below the filter.
Figure 3B:
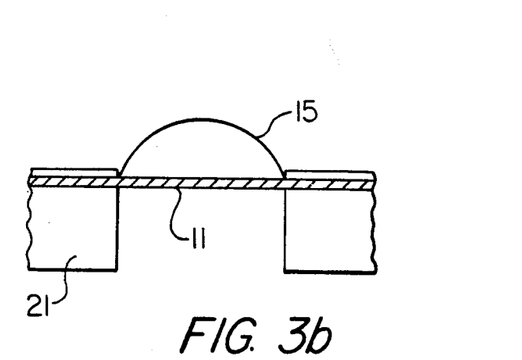
Figure 3C:
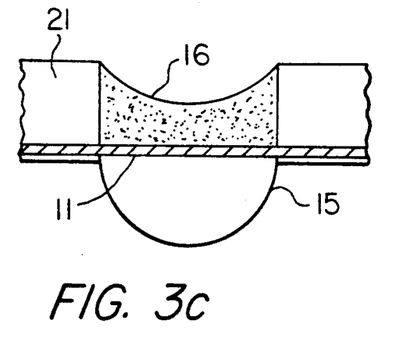
Figure 3D:
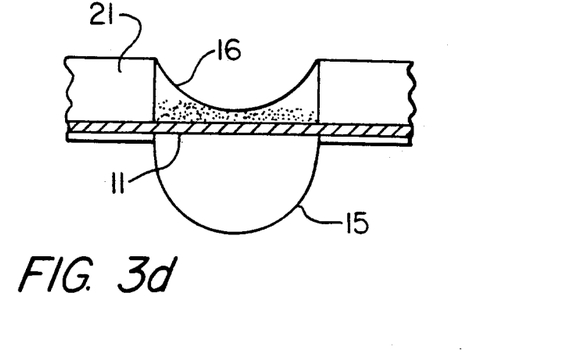

In a second preferred embodiment of the present invention, shown schematically in FIGS. 3a–3d, the apparatus also includes a grid 21 containing an array of holes 22. FIG. 3a also shows an optional patterned hydrophobic coating 23 on filter 11. FIG. 3b shows the apparatus after chemotactic factor or control 15 has been added. FIGS. 3c and 3d show the apparatus after it has been turned over, and a cell suspension 16 has been added. FIG. 3c shows the initial disposition of cell suspension 16, and FIG. 3d shown the disposition of cell suspension 16 after it has stabilized, when the gravitational forces are equalled by surface tension forces.

Grid 21 may be manufactured from any rigid or flexible material that is not biologically active or water-soluble, e.g., plastics such as acrylic, polystyrene, polycarbonate, polyethylene, or polypropylene; silicone; or metals such as coated aluminum, steel, or stainless steel. In this embodiment, for example, the holes may be placed in a 9 mm center-to-center pattern composed of 12 rows and 8 columns—the standard microtiter configuration. They may be arranged in any convenient pattern, however, on smaller or larger frames with a greater or lesser number of test sites. For example, when the final counting will be done using a microscope, the test sites could be arranged on a smaller frame, e.g., 2"×3" in a pattern closer than the 9 mm center-to-center pattern of the standard microtiter plate. In this preferred embodiment, the holes can vary in diameter from 0.5 mm to 7 mm. The optimum grid thickness depends upon the diameter of the holes, and the material of the grid. If the grid material is hydrophilic (or possibly if the grid material is neither hydrophilic nor hydrophobic) and the holes are 1 mm in diameter, the grid could be 0.5 mm thick. Capillary forces would then hold a large proportion of the fluid above the filter, as shown in FIG. 3d. If the grid material is hydrophobic, then the fluid may all be forced through the filter, as shown in FIG. 2d. If the wells were 6 mm in diameter and the grid material were hydrophilic or neutral, the grid material should be thicker to hold enough fluid above the filter to allow the concentration gradient of the chemotactic factor to develop.

Figure 4A:
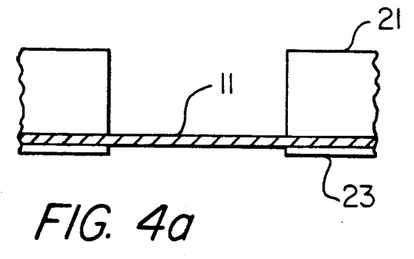
FIGS. 4a-4d are schematic representations of a third embodiment of the present invention showing the use of a grid positioned above the filter.
Figure 4B:
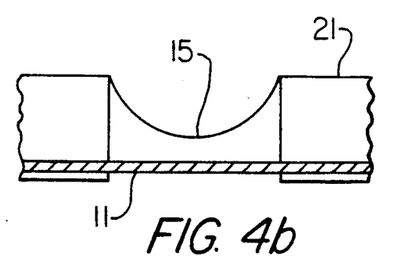
Figure 4C:
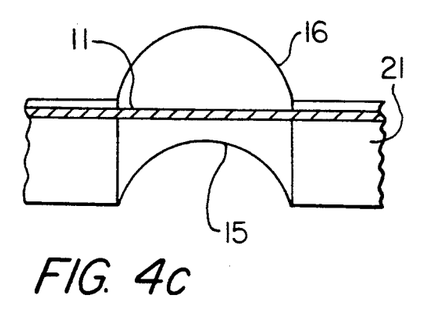
Figure 4D:
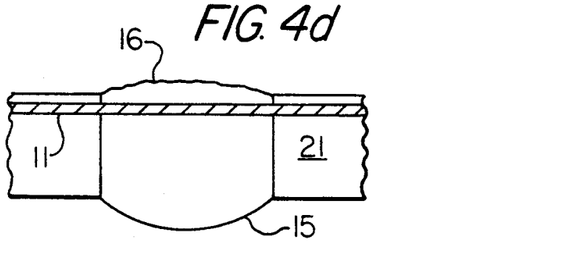

In a third embodiment of the present invention, shown in FIGS. 4a–4d, filter 11 is attached to the bottom of grid 21. FIG. 4a shows an optional patterned hydrophobic coating 23 on filter 11. FIGS. 4a–4d show the disposition of the chemotactic fluid 15 (FIGS. 4b, 4c and 4d) and cell suspension 16 (FIGS. 4c and 4d). FIG. 4c shows the disposition of the fluids immediately after the cell suspension is added, and FIG. 4d shows the disposition of the fluids after stabilization.

Figure 5A:
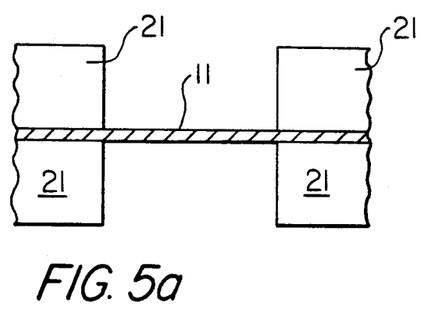
FIGS. 5a-5d are schematic representations of a fourth embodiment of the present invention showing the use of grids positioned both below and above the filter.
Figure 5B:
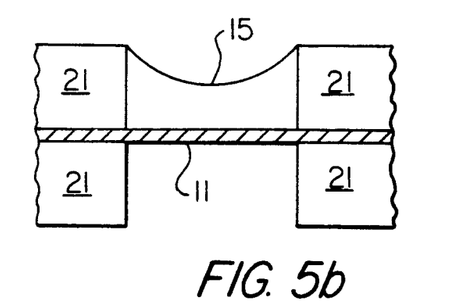
Figure 5C:
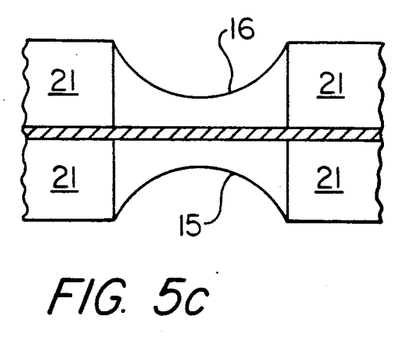
Figure 5D:
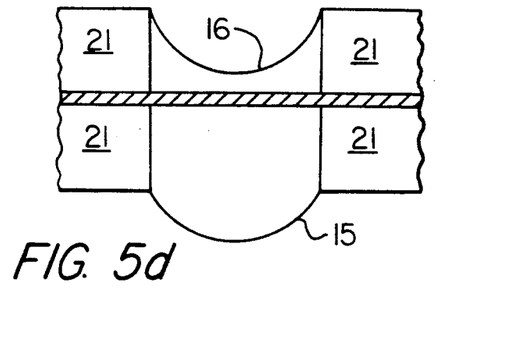

In a fourth embodiment of the present invention, two grids are used, as shown in FIGS. 5a–5d. One grid 21 is attached to the top of filter 11, and one grid 21 is attached to the bottom of filter 11. Chemotactic factors or controls 15 are added to one side of filter 21, as shown in FIG. 5b, and cell suspensions 16 are added to the other side of filter 11, as shown in FIG. 5c. FIG. 5c shows the disposition of the cell suspension initially. FIG. 5d shows the disposition of the fluids after stabilization.

Figure 6:
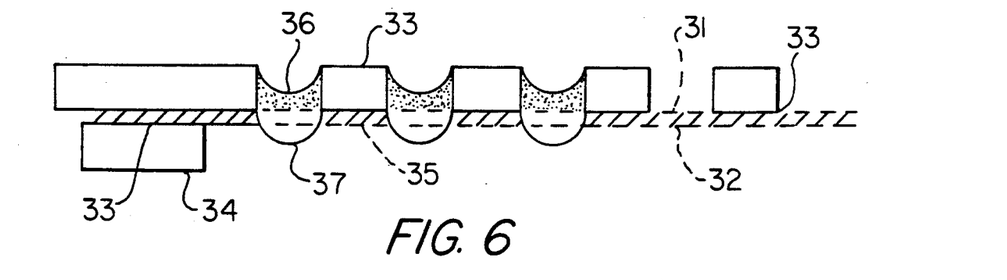
FIG. 6 is a schematic representation of a fifth embodiment of the present invention showing an apparatus constructed from two filters bonded to each other with a removable seal.

A fifth embodiment of the present invention uses two capillary pore membrane filters 31 and 32, as shown in FIG. 6, or one capillary pore membrane and one noncapillary pore membrane, or two noncapillary pore membranes. Filters 31 and 32 are each permanently bonded to grid 33 and outer frame 34, respectively. Filters 31 and 32 face each other, and are in direct contact with each other. FIG. 6 shows a gap between filters 31 and 32 only to make FIG. 6 more easily understood. The filters are temporarily bonded to each other by means of, for example, a thin pressure sensitive adhesive seal 35. The filters are sealed around each chemotaxis test site where cell suspensions 36, and controls and chemotactic factors 37 are to be positioned.

The chemotactic activity of the chemotactic factors is then determined according to the following procedure. First, the chemotaxis apparatus is inverted and chemotactic factors and controls 37 are placed on filter 32 opposite to the openings in grid 33. Second, the apparatus is placed right side up, and cell suspensions 36 are placed on filter 31 within the openings in grid 33.

Capillary action will hold most of the fluid in the top compartment, at which point a concentration gradient of the chemotactic factor will be established in those test sites containing chemotactic factors. Third, the apparatus is placed in an incubator. Fourth, the apparatus is removed from the incubator after incubation at about 37° C. for, e.g., 30 minutes to 72 hours. The cells are then fixed, and the top grid and filter are separated from the bottom frame and filter. Fifth, the bottom filter is stained. Finally, the number of cells on the bottom filter is counted.

Depending upon the kind of filter employed for the bottom filter, and on the counting technique (optical, densitometry, etc.) different methods would be used to handle the bottom filter after its separation from the top filter. For example, if a capillary pore polycarbonate filter is to be used, the filters can be separated before or after fixing and the cells and/or cellular debris on the top side of the bottom filter can be removed or not removed. If a standard optical technique is to be used to count the cells attached to the bottom filter, it may be desirable to remove cells and cellular debris from the top surface of the bottom filter. However, that would not be necessary if densitometry is to be used.

Figure 7:
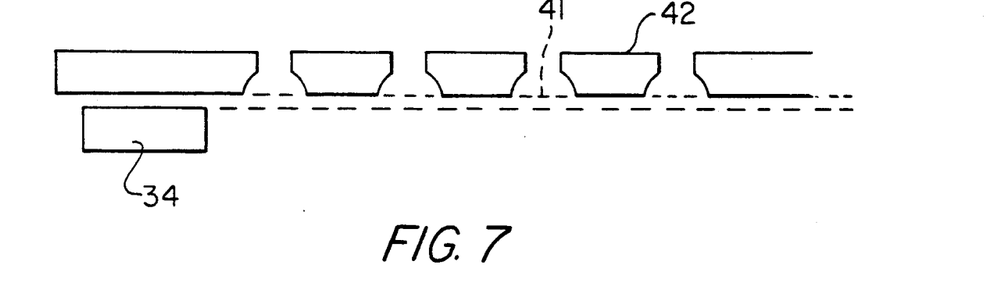
FIG. 7 is a schematic representation of a sixth embodiment of the present invention that utilizes specially shaped holes in a grid to control gravity flow.

A sixth preferred embodiment of the present invention, shown in FIG. 7, uses the same structure as the fifth embodiment, i.e. two membrane filters 41, one mounted on grid 42, the second to frame 34, and attached in direct contact to each other. However, in this embodiment, the holes in the grids are specially shaped to increase the amount of fluid held by capillary action in the top and bottom compartments after fluid stabilization. For example, as shown in FIG. 7, the opening of each hole in grid 42 is relatively narrow, with the diameter of the hole increasing towards filter 41.

Figure 8A:
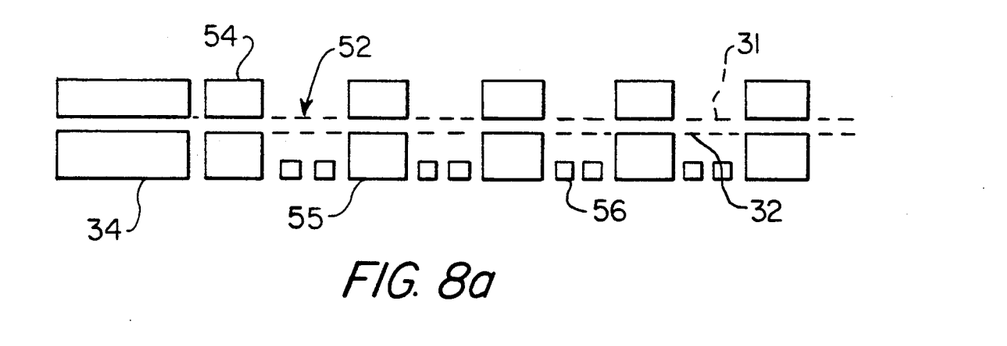
FIGS. 8a-8b are schematic representations of a seventh embodiment of the present invention incorporating specially shaped holes in a grid to control gravity flow.
Figure 8B:
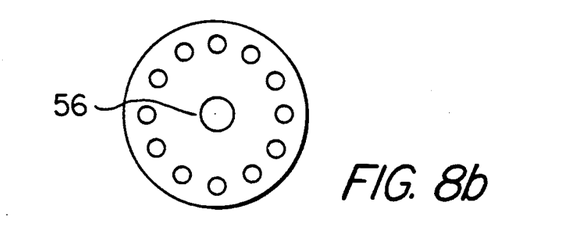

A seventh preferred embodiment shown in FIGS. 8a and 8b. This embodiment is similar to the sixth embodiment, but top grid 54 comprises relatively large holes 52, whereas bottom grid 55 comprises numerous smaller holes 56 corresponding to each larger hole 52 in top grid 54. FIG. 8a shows a cross-section of the apparatus viewed from the side. FIG. 8b is a view from the bottom of bottom grid 55, showing the disposition of small diameter holes 56 in bottom grid 55. The small diameter holes provide larger capillary action forces, more effectively counteracting the effect of gravitational forces on the fluids. An alternative to this embodiment comprises one grid with small holes that preclude gravity flow on the chemotactic factor side of the filters (usually the bottom side) and a hydrophobic coating (but no deep grid) on the other side (usually the bottom side). This configuration allows a drop of cell suspension to sit on top of a flat filter and not flow through at all (or very little), so that the concentration gradient is established immediately. Because there is plenty of fluid with the cells, the concentration gradient does not disappear rapidly. Also, the top surface can be easily wiped clean of cells that have not migrated.

An eighth preferred embodiment of the present invention also uses the same structure as the fifth embodiment, i.e., two capillary pore membrane filters mounted on grids and attached in direct contact to each other. In this embodiment, a flexible pressure sensitive sheet is used to seal off one side of a grid after its compartments are filled, or partially filled. The sheet limits gravity-induced flow when fluid is added to the other side of the filter, thus establishing a stable concentration gradient.

Figure 9A:
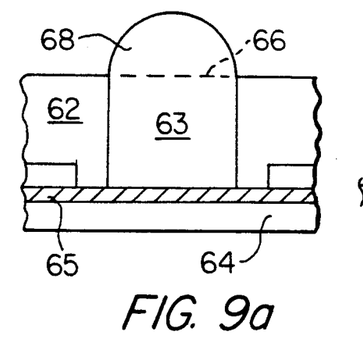
FIGS. 9a-9b are schematic representations of a ninth embodiment of the present invention incorporating a pressure-sensitive adhesive-backed sheet.
Figure 9B:
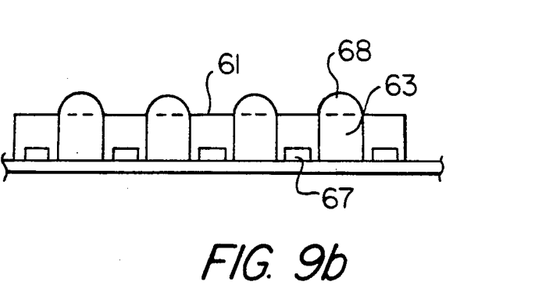

A ninth preferred embodiment of the present invention is similar to the eighth embodiment, but uses a single filter, as shown in FIGS. 9a-9b. This embodiment is used by filling the test sites formed by holes 61 in grid 62 with cell suspensions 63. A sheet 64 backed with a pressure sensitive adhesive 65 is applied to the side of grid 62 opposite to filter 66. Excess cell suspension is expressed and trapped in the recesses 67 between the test sites, and the apparatus is inverted. A chemotactic factor 68 is then pipetted onto the opposite side of the filter over each of the wells. The apparatus is then inverted again and incubated. Since the top test sites are sealed, the media in which the cells are suspended cannot flow through the filter upsetting the concentration gradient. Another way to use this apparatus would be to put the chemotactic factor(s) and control(s) in the side to be sealed, then pipette the cell suspension onto the other side.

Figure 10A:
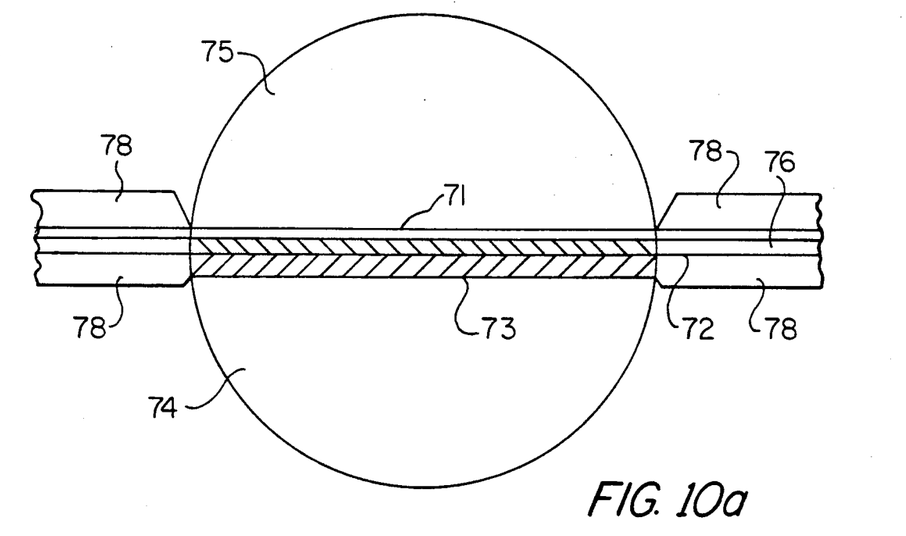
FIGS. 10a-10b are schematic representations of a tenth embodiment of the present invention incorporating a material that blocks fluid flow but allows diffusion of chemotactic factors and migration of cells.
Figure 10B:
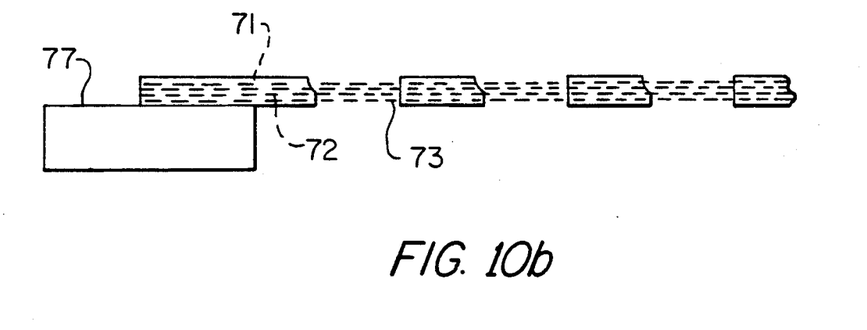

A tenth preferred embodiment of the present invention, which can use either two filters (as in the eighth preferred embodiment) or a single filter (as in the ninth preferred embodiment) is shown in FIGS. 10a-10b (two filter version). FIG. 10a is a cross-sectional side view of an individual chemotaxis test site. FIG. 10b is a cross-sectional side view of several chemotaxis test sites. FIG. 10a shows a top filter 71 and a bottom filter 72 placed close together facing each other, separated by a small space (5-20 micrometers). The pores of the filter(s) and the space between the filters (if two filters are used) are filled with an occluding material 73 such as agar, matragel (available from Collaborative Research) that will allow diffusion of chemotactic factors 74 and migration of the cells in cell suspension 75, and will not dissolve in media (or will dissolve slowly enough to allow the assay to be completed). The two filters are kept close together by a removable pressure sensitive adhesive 76 that surrounds each well. The assembly is supported by an outer frame 77, as shown in FIG. 10b. The apparatus is similar to the apparatus of the eighth preferred embodiment (if two filters are used) or to the ninth preferred embodiment (if a single filter is used). Gravity does not affect the fluids since the agar (or equivalent occluding material) prevents the vertical flow of the fluids. If two filters are used, capillary pore filters are preferred since melted agarose will flow between the two filters by capillary action, leaving no voids. Horizontal flow is prevented by a relatively hydrophobic coating 78 surrounding each well.

In an eleventh preferred embodiment of the present invention, the two-filter structure disclosed in the fifth embodiment is used, but the pressure-sensitive adhesive is soluble in a solvent such as ethanol that does not dissolve the filters. The two filters could then be easily separated after the apparatus is soaked in, for example, ethanol fixative. Alternatively, the top filter could be made from a material (e.g., cellulose nitrate) that dissolves in a solvent (e.g., ethanol), and the bottom filter could be made from a material (e.g., polycarbonate) that does not dissolve in that solvent. The top filter would then be dissolved in the solvent after the cells are fixed, or during the fixing process. In either alternative, after the bottom filter is separated from the top filter, the bottom filter would be stained and the number of cells on or in the bottom filter would be determined using any of the techniques discussed above.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A method for performing chemotactic tests comprising:
   (a) providing at least one membrane filter having a top and bottom side;
   (b) placing drops of chemotactic factor at a first set of preselected locations on the top side of said at least one membrane filter;
   (c) placing drops of controls at a second set of preselected locations on the top side of said at least one membrane filter;
   (d) turning said at least one membrane filter over such that the top side of said at least one membrane filter is now considered the bottom side of the at least one membrane filter wherein the chemotactic factors and controls are now on the bottom side of said at least one membrane filter;
   (e) placing drops of cell suspensions on the top side of said at least one membrane filter, said drops of cell suspensions being placed opposite to the drops of chemotactic factors and controls;
   (f) waiting an amount of time sufficient to allow the surface tension forces to equal the gravitational forces, thus stabilizing the chemotactic factors, controls, and cell suspensions and allowing a concentration gradient of the chemotactic factor to form;
   (g) incubating said at least one membrane filter; and
   (h) determining the response of the cell suspensions to the chemotactic factor concentration gradients and the controls.

2. The method of claim 1, wherein said at least one membrane filter includes a pattern on the surfaces of the at least one membrane filter defining the positions of the first and second set of preselected locations.

3. The method of claim 2, wherein the pattern is formed by a technique selected from the group consisting of imprinting ink on the filter and applying a coating on the at least one membrane filter.

4. The method of claim 2, wherein the pattern is formed by applying a hydrophobic coating on the at least one membrane filter.

5. The method of claim 1, wherein said at least one membrane filter is a capillary pore membrane filter.

6. The method of claim 1, wherein the at least one membrane filter is a single membrane filter.

7. The method of claim 6, wherein the single membrane filter is attached to a grid having holes, and wherein the first and second set of preselected locations correspond to the position of holes in the grid.

8. The method of claim 7, wherein the membrane single filter has a hydrophobic coating having openings corresponding to the first and second set of preselected locations.

9. The method of claim 7, wherein after the drops of cell suspensions are placed in the holes in the grid, a sheet backed with a pressure sensitive adhesive is applied to the side of the grid opposite to the single membrane filter.

10. The method of claim 7, wherein after the drops of chemotactic factors and controls are placed in the holes in the grid, a sheet backed with a pressure sensitive adhesive is applied to the side of the grid opposite to the filter.

11. The method of claim 7, wherein pores of the single membrane filter contain an occluding material that does not prevent migration of the cells and does not prevent diffusion of the chemotactic factors.

12. The method of claim 6, wherein a first grid is attached to the top of the single membrane filter, and a second grid is attached to the bottom of the single membrane filter.

13. The method of claim 12, wherein the single membrane filter further includes a hydrophobic coating having openings corresponding to the first and second set of preselected locations.

14. The method of claim 12, wherein pores of the single membrane filter contain an occluding material that does not prevent migration of the cells.

15. The method of claim 1, wherein the at least one membrane filter are two membrane filters.

16. The method of claim 15, wherein each membrane filter is attached to its own grid, wherein the grids have holes at positions corresponding to the first and second set of preselected locations and wherein the two membrane filters face each other and are temporarily bonded to each other.

17. The method of claim 16, wherein the holes in the grids are especially shaped to increase the amount of chemotactic factors, controls and cell suspensions held therein by capillary action.

18. The method of claim 17, wherein the diameters of the holes increase towards the two membrane filters.

19. The method of claim 17, wherein one grid comprises at least three smaller holes each corresponding to a larger hole in the other grid.

20. The method of claim 16, wherein a pressure sensitive sheet is applied to seal off one side of a grid after chemotactic factors and controls have been placed in the holes in the grid.

21. The method of claim 16, wherein a pressure sensitive sheet is applied to seal off one side of a grid after cell suspensions have been placed in the holes in the grid.

22. The method of claim 16, wherein pores of the two membrane filters contain an occluding material that does not prevent migration of the cells and does not prevent diffusion of the chemotactic factor.

23. The method of claim 15, wherein the two membrane filters are attached to each other with a pressure-sensitive adhesive.

24. The method of claim 23, wherein the pressure-sensitive adhesive is soluble in a solvent that does not dissolve the two membrane filters.

25. The method of claim 15, wherein one membrane filter is made from a material that dissolves in a solvent, and the other membrane filter is made from a material that does not dissolve in the solvent, and the membrane filter that dissolves in the solvent is dissolved in the solvent after incubation.

26. A chemotactic apparatus comprising:
   (a) at least one membrane filter having a top and bottom side and further having a pattern on the surfaces of the at least one filter defining the positions of a first and second set of preselected locations;
   (b) drops of chemotactic factor located at the first set of preselected locations on the top side of said at least one membrane filter;

(c) drops of controls located at the second set of preselected locations on the top side of said at least one membrane filter; and (d) drops of cell suspensions located on a side of said at least one membrane filter opposite to the side having the chemotactic factors and controls, said drops of cell suspensions being juxtaposed to the drops of chemotactic factors and controls.

27. The chemotactic apparatus of claim 26, wherein the pattern comprises imprinted ink on the filter at least one membrane.

28. The chemotactic apparatus of claim 26, wherein the pattern comprises an applied hydrophobic coating on the at least one membrane filter.

29. The chemotactic apparatus of claim 26, wherein said at least one membrane filter is a capillary pore membrane filter.

30. The chemotactic apparatus of claim 26, wherein the at least one membrane filter is a single membrane filter.

31. The chemotactic apparatus of claim 26, wherein the at least one membrane filter are constructed of two membrane filters.

32. The chemotactic apparatus of claim 26, wherein the pattern comprises a patterned plastic coating on the at least one membrane filter.

33. The chemotactic apparatus of claim 26, wherein the pattern comprises a patterned silicone coating on the at least one membrane filter.

34. A chemotactic apparatus comprising:
(a) at least one membrane filter having a top and a bottom surface;
(b) a grid having holes, said grid being attached to either one of the top surface and the bottom surface of each of said at least one membrane filter;
(c) drops of chemotactic factor located on said at least one membrane filter inside a first preselected set of holes in said grid;
(d) drops of controls located on said at least one membrane filter inside a second preselected set of holes in said grid; and
(e) drops of cell suspensions located on a side of said at least one membrane filter opposite to the side having the chemotactic factors and controls, said drops of cell suspensions being located opposite to the drops of chemotactic factors and controls.

35. The chemotactic apparatus of claim 34, wherein the at least one membrane filter further comprises a hydrophobic coating having openings corresponding to the first and second set of preselected holes in said grid.

36. The chemotactic apparatus of claim 34, further comprising a sheet backed with a pressure sensitive adhesive applied to the side of a grid opposite to the side of the grid to which the at least one membrane filter is attached, said at least one membrane filter bearing the drops of cell suspensions.

37. The chemotactic apparatus of claim 34, further comprising a sheet backed with a pressure sensitive adhesive applied to the side of a grid opposite to the side of the grid the at least one membrane filter is attached to, said at lease one membrane filter bearing the drops of chemotactic factors and controls.

38. The chemotactic apparatus of claim 34, wherein the at least one membrane filter are constructed of two membrane filters and one grid having holes is attached to each membrane filter.

39. The chemotactic apparatus of claim 38, wherein the holes in the grids are specially shaped to increase the amount of chemotactic factors, controls and cell suspensions held therein by capillary action.

40. The chemotactic apparatus of claim 39, wherein the diameters of the holes increase towards the membrane filters.

41. The chemotactic apparatus of claim 39, wherein at least one grid comprises at least three smaller holes corresponding to each site on the membrane filter.

42. The chemotactic apparatus of claim 38, further comprising a pressure sensitive sheet sealing off the holes of one side of one of the grids, said holes of that grid containing the drops of chemotactic factors or controls.

43. The chemotactic apparatus of claim 38, further comprising a pressure sensitive sheet sealing off one side of one of the grids, said holes of that grid containing cell suspensions.

* * * * *